United States Patent
Ness et al.

(10) Patent No.: US 6,194,375 B1
(45) Date of Patent: Feb. 27, 2001

(54) COMPOSITIONS CONTAINING PERFUME

(75) Inventors: Jeremy Nicholas Ness, Ashford;
Pamela Virginia Irving, Folkestone;
Marcus James Goodall, Ashford, all of (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 08/996,721

(22) Filed: Dec. 23, 1997

(30) Foreign Application Priority Data

Dec. 23, 1996 (EP) .................................... 96309466

(51) Int. Cl.[7] .............................. A61K 7/46; A61K 7/06; A61K 9/48; C11D 9/44

(52) U.S. Cl. ................... 512/4; 512/2; 424/70.1; 424/70.11; 424/451; 510/108; 510/119; 510/349; 510/515; 510/519

(58) Field of Search ................. 512/2, 4; 424/70.1, 424/70.11, 451; 510/108, 119, 349, 515, 519

(56) References Cited

U.S. PATENT DOCUMENTS

| 4,234,627 | * | 11/1980 | Schilling | 427/242 |
|---|---|---|---|---|
| 4,842,761 | * | 6/1989 | Rutherford | 252/90 |
| 4,908,233 | * | 3/1990 | Takizawa et al. | 427/213.35 |
| 5,051,305 | * | 9/1991 | Whitaker, Sr. | 428/402.2 |
| 5,112,688 | * | 5/1992 | Michael | 428/402.2 |
| 5,154,842 | * | 10/1992 | Walley et al. | 252/8.6 |
| 5,180,637 | * | 1/1993 | Sumii | 428/402.21 |
| 5,188,753 | * | 2/1993 | Schmidt et al. | 252/132 |
| 5,281,355 | * | 1/1994 | Tsaur et al. | 252/174.13 |
| 5,281,357 | * | 1/1994 | Morgan et al. | 252/174.13 |
| 5,336,665 | * | 8/1994 | Garner-Gray et al. | 512/4 |

FOREIGN PATENT DOCUMENTS

| 0 266 796 | * | 5/1988 | (EP) . |
|---|---|---|---|
| 0 590 538 | * | 6/1994 | (EP) . |
| 1390503 | * | 4/1975 | (GB) . |
| WO 98/12298 | * | 3/1998 | (WO) . |
| WO 98/28339 | * | 7/1998 | (WO) . |

* cited by examiner

Primary Examiner—Jill Warden
Assistant Examiner—Monique T. Cole
(74) Attorney, Agent, or Firm—Pillsbury Madison & Sutro LLP

(57) ABSTRACT

Perfume is absorbed within organic polymer particles which have a further polymer at their exterior. The further polymer incorporates free hydroxyl groups and serves to promote deposition of the particles from a wash or rinse liquor. The further polymer may be part of an encapsulating shell, but more conveniently is used as a stabilizer during polymerization of the particles. Highly hydrolyzed polyvinyl alcohol is preferred.

25 Claims, No Drawings

COMPOSITIONS CONTAINING PERFUME

This invention relates to detergent compositions and other fabric treatment compositions, including personal washing and hair-conditioning compositions, laundry detergent compositions and rinse conditioner compositions for fabric softening.

SUMMARY OF THE PRIOR ART

There have been a number of proposals for absorbing perfume onto a solid carrier material, and various reasons for doing so. In a number of instances, the objective of such proposals has been merely to convert liquid perfume into a solid form which can more readily be incorporated into another product. It has been asserted that such carrier substances may serve to protect the perfume from loss during storage or protect it from contact with other constituents of a composition.

Examples of disclosures of such carriers for perfume are GB-A-1306924, U.S. Pat. No. 3,449,266 U.S. Pat. No. 3,909,461 U.S. Pat. No. 4,536,315, U.S. Pat. No. 4,539,135, U.S. Pat. No. 4,713,193, GB-A-2066839, EP-A-332259, EP-A-332260 and JP-A-63/79662. In many of these documents the carriers are inorganic materials.

EP-A-535942 and EP-A-536942 are concerned with inorganic carrier materials which serve to reduce the vapour pressure of absorbed perfume.

As pointed out in those documents, a carrier material which reduces the perfume vapour pressure over the solid carrier but releases the perfume on contact with water can be useful to avoid giving excessive perfume odour to a concentrated product, yet provide the required concentration of perfume in a wash or rinse liquor.

EP-A-285694 is one of a series of documents concerned with porous cross linked polymers obtained by polymerisation around droplets of a liquid substance which may subsequently be removed. These porous polymers can act as carriers for a variety of liquids. They are used in products for application to the skin, and give controlled release of the liquid to the skin.

U.S. Pat. No. 4,842,761 discloses composite particles in which one polymer is embedded within another. These particles are used as perfume carriers in laundry detergents and provide controlled release of perfume.

THE INVENTION

We have now found that the deposition of perfume from a composition having an active ingredient can be improved by incorporating the perfume into particles containing organic polymer, and providing at the surface of the particles a further polymer with free hydroxyl groups. Such polymer enhances deposition of the particles and by doing so also enhances deposition of the perfume. The use of such particles can enhance deposition of perfume, or components thereof; it can retard the evaporation of deposited perfume and can also enhance the extent to which deposited perfume survives a subsequent drying step.

Accordingly, the present invention provides a product which is an article or composition containing an active ingredient which is a detergent active, a fabric softening agent or a hair conditioning agent, and particles containing organic polymer which are insoluble in water and carry perfume, carried by a core of the particle, and at the exterior of the core a further polymer attached to the core so as not to be removed therefrom in water, which further polymer incorporates free hydroxy groups and is present in a quantity which is no more than 25% of the weight of the particles. This further polymer will be referred to below as a "hydroxy functional polymer".

The quantity of the particles in the products will depend on the nature of the product but will generally provide perfume in an amount within the broad range 0.1 to 10% by weight. In particular such products may be personal washing compositions, fabric detergent compositions, other cleaning compositions and fabric or hair conditioner compositions incorporating such perfume-containing particles.

As will be explained in greater detail below, the organic polymer particles may be polymer capsules which enclose perfume or may be solid (but possibly porous solid) particles into which perfume is absorbed. Polymer capsules may enclose liquid perfume or a solid core into which perfume is absorbed.

The particles themselves are insoluble in water, so that they can be deposited from an aqueous wash or rinse liquor.

The hydroxy functional polymer at the exterior of these particles may form, or be included within a coating or incomplete coating on these individual particles. The hydroxy functional polymer is preferably nonionic or cationic. It will be explained below that it generally constitutes between 1 and 25% of the weight of the perfume-containing particles, usually between 1 and 10%. Cationic functionalities may additionally be present at the exterior of the particles, and may be provided by the hydroxy functional polymer or otherwise. Presence of cationic monomers has a tendency to increase particle size.

Particle Size

Polymer particles used in this invention desirably have an average particle size of at least 1 $\mu$m, better at least 20 $\mu$m or 30 $\mu$m, for ease of handling. Also, we have observed that the rate of release of fragrance may be faster than desired if the particles are of very small size such as average size of 1 $\mu$m. The polymer particles desirably have an average size not larger than 150 $\mu$m, better not over 125 $\mu$m so that the particles are not easily visible after deposition.

For particles intended to be used in fabric washing or conditioning, it is especially preferred to use particles with a mean size of at least 40 $\mu$m, e.g. 40 to 100 $\mu$m to retain perfume in the particles and provide slow perfume release.

For particles intended for other products, e.g. personal washing products, a faster rate of release may be desired than with fabrics products, although retention of perfume and delay in release for some hours is still desirable, consequently a smaller particle size may be advantageous, such as a mean size in the range from 10 to 50 $\mu$m.

Polymerisation techniques generally produce a range of particle sizes. For this invention it is desirable that a high proportion of the particles lie between the above limits on particle size. Thus, when particles are intended for fabric treatment, preferably 90% or more of the particles are larger than 30 $\mu$m. Preferably also 90% or more of the particles are not larger than 150 or even 125$\mu$. Better, 95% or more are not larger than 125 or even 100 $\mu$m.

To achieve these criteria, it may be necessary to sieve the particles and thereby separate oversized and/or undersized particles. An important aspect of reducing the amount of emulsion polymer formed (broadly speaking, polymer beads of a size below 10 $\mu$m) is to use an initiator system that is substantially insoluble in the aqueous phase, so as to prevent initiation of monomer molecules held in micelles. Suitable water insoluble initiators include azo compounds such as azobisisobutyronitrile (AIBN) and higher alkyl peroxides.

Hydroxy Functional Polymer

This polymer bearing hydroxy groups and located at the exterior of the particles serves to enhance deposition onto (or retention on) skin, hair, hard surfaces especially vitreous surfaces and fabric.

This polymer is desirably such that at least 80% of the monomer residues in the polymer contain at least one free hydroxy group able to participate in hydrogen bonding. The polymer is preferably nonionic and such that, in its pure state, it is water-soluble. However, when attached to the exterior of the particles, it does not render them water soluble. The attachment is such that the polymer is not completely removed upon contact with water. It may be chemically bonded with the core polymer.

The preferred polymer is polyvinyl alcohol.

As is well known, polyvinyl alcohol cannot be prepared directly by polymerisation, and is obtained by the hydrolysis of polyvinyl acetate. This hydrolysis generally stops before completion, and polymers with varying amounts of hydrolysis are commercially available.

We have found that deposition of particles, especially onto fabric, is better when the polyvinyl alcohol exhibits a substantial level of hydrolysis.

We may therefore prefer to use polyvinyl alcohol which is 85 to 100% hydrolysed i.e. in which 85 or 88 to 100% of the acetate residues have been removed by hydrolysis. More preferably, the polyvinyl alcohol is at least 90% better at least 96% hydrolysed, e.g. 96 to 99% hydrolysed.

Another possible polymer is a copolymer of polyvinyl alcohol, available through hydrolysis of the corresponding copolymer of vinyl acetate. For example a copolymer of vinyl acetate and vinyl formamide, with a high proportion of vinyl acetate can by hydrolysed to a copolymer of vinyl alcohol and vinyl formamide. Further hydrolysis of such a polymer converts the formamide residues to amine groups, giving a cationic copolymer of vinyl alcohol and vinyl amine.

Another category of polymers which can be used is cellulose and chemically modified cellulose where the modification does not greatly reduce the number of hydroxyl groups present. Examples of polymers in this category are hydroxyethyl cellulose, and hydroxypropyl cellulose.

Hydroxyethyl cellulose is available commercially and is made by treatment of cellulose with sodium hydroxide, followed by reaction with ethylene oxide. Another possibility is cellulose which has been chemically modified by the introduction of cationic substituent groups.

It is a characteristic of many grades of polyvinyl alcohol and of hydroxy ethyl cellulose that free hydroxy groups constitute more than 20%, often more than 25% of the weight of the polymer.

Solid Particles

For this invention it is preferred to use polymer particles which are solid—although they may be porous as well as solid—rather than particles in the form of hollow capsules.

Advantages of solid particles are that the desired size range is accessible, and that the polymerisation reaction can be carried out in the absence of perfume.

The particles could possibly be porous particles made by polymerisation around a liquid pore-forming agent, as taught in EP-A-285694. However, we have found it to be unnecessary to include such a pore-forming agent. Polymers formed by simple polymerisation of a monomer mixture are able to absorb and carry perfume.

Preferred polymer particles may be formed by the polymerisation of vinyl monomers, with some cross linking and/or chain branching agent included in the monomers which are polymerised, so that some cross links are formed between the polymer chains. If a cross linking agent is used, the proportion of cross linking may be low, so that after polymerisation there may be some polymer chains which remain entirely linear and are not cross linked to any other chains.

A number of vinyl monomers containing a single carbon-carbon double bond may be used. One suitable category of monomers is the esters of acrylic and alkyl acrylic acids, of formula 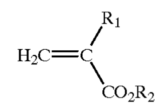 where $R_1$ is hydrogen or straight or branched alkyl of 1 to 6 carbon atoms, preferably 1 to 3 carbon atoms and $R_2$ is straight or branched alkyl of 1 to 6 or 8 carbon atoms, preferably 3 to 6 and most preferably 3 or 4 carbon atoms in a straight or branched chain.

Specific examples of suitable monomers are isobutyl methacrylate (which is particularly preferred), n-butyl acrylate, n-butyl methacrylate, isobutyl acrylate, n-propyl acrylate and iso-propylmethacrylate. Less preferred is methyl methacrylate.

Another suitable monomer is styrene.

It is possible to use simple linear polymers. However, these can give particles which are somewhat sticky, and it is usually convenient to introduce some cross-linking or chain branching.

Cross linking between polymer chains formed from the above monomers can be achieved by including in the monomer mixture a small proportion—for example less than 10%, preferably as little as 5% or 1%—of a monomer with two carbon-carbon double bonds. The use of such a material to provide cross linking is well known in other applications of polymers, although it is usual to introduce a greater proportion of cross linking than is required for this invention. Examples of this type of cross linking agent are divinyl benzene, diesters formed between acrylic acid and diols, such as 1,4 butane diol diacrylate, and higher esters formed between acrylic acid and polyols—which may be sugars.

Chain branching can be introduced by including among the monomers a hydroxyalkyl monomer of formula 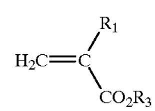 where $R_1$ is as specified above and $R_3$ is alkyl of 1 to 6 carbon atoms bearing at least one hydroxy group, preferably 3 to 4 carbon atoms in a straight or branched chain and bearing a single hydroxy group. These monomers undergo a side reaction during the course of polymerisation, and this side reaction produces chain branching. When there is chain branching without cross linking, it is suitable that hydroxyalkyl monomer of the above formula provides from 10 to 40% by weight of the monomer mixture.

Suitable hydroxyalkyl acrylate monomers are hydroxypropyl methacrylate, hydroxybutylacrylate, and hydroxyethylacrylate.

Attachment of a polymer with hydroxy groups, notably polyvinyl alcohol, at the exterior of the particles, can be achieved by polymerising the monomers in the presence of the polyvinyl alcohol (or other polymer with hydroxy groups) using the technique of suspension polymerisation.

Suspension polymerisation is a process in which the organic monomers are formed into a suspension in an aqueous phase, and polymerised. Polymerisation of each suspended droplet leads to a bead of polymer.

It is customary to stabilise the suspension by incorporating a stabilising agent in the aqueous phase before adding the monomer. Polyvinyl alcohol is known to act as a stabiliser.

Thus, a typical polymerisation procedure will commence by forming an aqueous solution of the hydroxy functional polymer which acts as stabilising agent, together with a polymerisation initiator, in a reaction vessel. Then while agitating the contents of the reaction vessel, the organic monomers are progressively fed in so that the monomers become dispersed in the aqueous phase and polymerise therein. The addition of monomers can be continued until the mixture in the reaction vessel is a slurry of polymer beads containing about 30% by weight of polymer.

In a possible variation of this procedure some of the monomer is dispersed in the aqueous solution of stabilising agent before any polymerisation initiator is added. In another possible variation the monomers are emulsified in water before they are added to the reaction vessel.

Suspension polymerisation typically produces polymer beads with a diameter larger than $100\mu$. Smaller particle sizes in the range of $50$–$100\mu$ can be obtained by increasing the amount of stabiliser in the aqueous phase, or by increasing the amount of agitation, or both.

Polymerisation may be carried out using a combination of polyvinyl alcohol and a second stabilising agent which may or may not be a second hydroxy-functional polymer. Examples of materials which can serve as a second stabilising agent include sodium oleate and sodium lauryl sulphate, both of which are anionic surfactants, also non-ionic surfactants with HLB of 8 and above, such as $C_{13}/C_{15}$ alcohol ethoxylated with 3 to 11 ethylene oxide residues, and sorbitan ester surfactants of similar HLB.

The amount of hydroxy functional polymer present in solution as a stabilising agent will generally be between 1% and 5% by weight of the aqueous phase in which polymerisation occurs. Larger amounts can also be used.

The amount may well be between 3% and 15% by weight of the monomers undergoing polymerisation, possibly between 5% and 10%.

Observation by microscopy of such particles showed the hydroxy functional polymer to form a coating or incomplete coating of the particles, from which it can be estimated that the amount of hydroxy functional polymer attached to the particles was at least 1% by weight of these particles after (and also of course before) the incorporation of perfume.

Suspension polymerisation can be used to produce linear polymers, or cross linked polymers. The presence or absence of cross linking is determined by the monomers which are used.

As mentioned above, a molecule with more than one carbon-carbon double bond can serve as a cross linking agent. When used, a suitable amount of such cross-linking agent is not over 5 mole % of the monomer mixture, e.g. in a range from 0.5 to 3 mole %.

Hydroxy substituted acrylate esters can also lead to cross-linking. The mechanism by which they do so is a side reaction which is not fully understood. When used, a suitable amount may lie in a range from 3 to 30 moles % of the monomer mixture. Preferably 10 to 30 mole %.

After the manufacture of the particles by polymerisation, the direct product is in the form of an aqueous slurry. If desired, the particles may be separated from the aqueous phase by filtration or centrifuging, possibly followed by drying.

Another possible route for the production of polymer particles is emulsion polymerisation to yield an aqueous emulsion of very small polymer particles (typically of sub-micron size) followed by a drying step to agglomerate these particles into larger particles with a size of at least $20\mu$.

Absorption of perfume by the particles can be brought about simply by bringing the perfume and the particles into contact, and allowing them to stand. This may be done by mixing perfume with the particles after they have been separated from the aqueous phase, or it may be done by mixing perfume into an aqueous slurry of the particles and allowing the mixture to equilibrate. It can be done by mixing the particles and perfume separately into an aqueous liquid product and allowing that mixture to equilibrate.

Encapsulation

An alternative to the use of solid particles of polymer is to form hollow capsules in which a shell of polymer encapsulates perfume.

One approach to the preparation of microcapsules of perfume is to disperse perfume droplets in an aqueous phase which contains water soluble polymer, and then form a polymer shell around these perfume droplets by coacervation of the polymer at the interface between the perfume and the aqueous phase. Once the capsule wall has been formed, it usually requires further treatment to strengthen it.

The encapsulation of perfume by coacervation has been described by Meyer, A in Chimica, 46 101 (1992) and in U.S. Pat. No. 5,051,305.

A second approach to the formation of microcapsules of perfume is to disperse perfume droplets in an aqueous phase, and then bring about a polymerisation reaction at the interface between the droplets and the aqueous phase. The polymerisation reaction which has mostly been employed is the formation of an aminoplast resin.

This has been used for perfume encapsulation, as disclosed in U.S. Pat. No. 4,681,806.

A typical procedure for the production of aminoplast resin capsules enclosing perfume is set out in U.S. Pat. No. 4,234,627, which refers back to U.S. Pat. No. 3,516,941.

Capsules with polyvinyl alcohol (or other polymers with hydroxy groups) at their exterior can be made by carrying out the aminoplast polymerisation in the presence of the hydroxy functional polymer.

Thus a typical procedure would be to form an aqueous solution containing this hydroxy functional polymer and also from 3 to 30% by weight of a urea-formaldehyde precondensate (methylol urea). Next, water-insoluble liquid perfume is dispersed throughout this solution and rapidly agitated to keep it dispersed in the form of discrete droplets. While maintaining solution temperature between 20° C. and 90° C., acid is then added to catalyse polymerisation of the dissolved urea-formaldehyde precondensate. If the solution is rapidly agitated during this polymerisation step, shells of water-insoluble, urea-formaldehyde polymer form around and encapsulate the dispersed droplets of perfume, and molecules of the hydroxy-group containing polymer are incorporated in and at the exterior of these shells. Melamine-formaldehyde precondensate can be used in place of urea-formaldehyde, and may be preferred.

The hydroxy functional polymer may constitute a substantial part of the polymer shell which encapsulates the perfume, but this shell will typically be outweighed by perfume, so that the hydroxy functional polymer provides from 1% to 25% by weight of the perfume-containing capsules.

Encapsulated Particles

A further possibility is to encapsulate a "core" of polymer as described above, with aminoplast resin, while providing hydroxy-functional polymer at the exterior of the capsules, and absorb perfume within the core.

Several typical procedures are available to produce such encapsulated polymer. One procedure is to form polymer beads, for example of an acrylate polymer, as described earlier, and dispense this organic mixture in an aqueous solution containing the hydroxy functional polymer and urea-formaldehyde precondensate. The mixture is agitated to keep the organic mixture in suspension. While maintaining solution temperature between 20° C. and 90° C., acid is then added to catalyse polymerisation of the dissolved urea-formaldehyde precondensate. If the solution is rapidly agitated during this polymerisation step, shells of water-insoluble, urea-formaldehyde polymer form around and encapsulate the dispersed organic mixture and molecules of the hydroxy-group containing polymer are incorporated in and at the exterior of these shells. Melanine-formaldehyde precondensate can be used in place of urea-formaldehyde, and may be preferred.

Another procedure is to form encapsulated core polymer, in the absence of perfume, and subsequently allow perfume to diffuse through the shell, into the core polymer. We have found that absorption of perfume is possible through a thin shell, even though a thicker hollow shell is capable of retaining liquid perfume. Suitably the weight of polymer forming the shell is less than the weight of polymer forming the core, and the shell to core weight ratio may lie in a range from 1:3 to 1:20, better 1:5 to 1:20.

Hydroxy functional polymer will generally provide a substantial proportion of the shell, yet constitute from 1% to 25% of the capsules.

For this procedure it has been found preferable to encapsulate monomer within an aminoplast shell, then polymerise the monomer to form a (preferably solid) core of polymer within the shell. Less preferred is to partially polymerise the core before encapsulation.

It is also possible to encapsulate a mixture of liquid monomer and fragrance, then polymerise. However, this necessarily exposes perfume to the polymerisation reaction, whereas absorption of perfume through the shell into a previously polymerised core does not.

When a product contains particles in which perfume is absorbed within polymer which is encapsulated by a thin shell, perfume can diffuse through the shell, and can be released without rupture of the shell, although the release and dispersion of perfume will be slower than for neat perfume. Thus, encapsulated polymer with absorbed perfume can provide deposition and retarded release of perfume similarly to the (preferred) arrangement when perfume is absorbed in polymer beads which have hydroxy functional polymer directly at their exterior.

Perfume

As is well known, a perfume normally consists of a mixture of a number of perfumery materials, each of which has a fragrance. The number of perfumery materials in a perfume is typically ten or more. The range of fragrant materials used in perfumery is very wide; the materials come from a variety of chemical classes, but in general are water-insoluble oils. In many instances, the molecular weight of a perfumery material is in excess of 150, but does not exceed 300.

The perfumes used in the present invention can be mixtures of conventional perfumery materials. Perfumery materials which may be used include: acetyl cedrene, 4-acetoxy-3-pentyltetrahydropyran, 4-acetyl-6-t-butyl-1,1-dimethylindane, available under the trademark "CELESTOLIDE", 5-acetyl-1,1,2,3,3,6-hexamethylindane, available under the trademark "PHANTOLIDE", 6-acetyl-1-isopropyl-2,3,3,5-tetramethylindane, available under the trademark "TRASEOLIDE", alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl)propanal, 4-t-butylcyclohexyl acetate, 4-t-butyl-3,5-dinitro-2,6-dimethyl acetophenone, 4-t-butylcyclohexanol, benzoin siam resinoids, benzyl benzoate, benzyl acetate, benzyl propionate, benzyl salicylate, benzyl isoamyl ether, benzyl alcohol, bergamot oil, bornyl acetate, butyl salicylate, carvacrol, cedar atlas oil, cedryl methyl ether, cedryl acetate, cinnamic alcohol, cinnamyl propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-1-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethylbenzylcarbinol, dimethylheptanol, dimethyloctanol, dimyrcetol, diphenyl oxide, ethyl naphthyl ether, ethyl vanillin, ethylene brassylate, eugenol, geraniol, geranium oil, geranonitrile, geranyl nitrile, geranyl acetate, 1,1,2,4,4,7-hexamethyl-6-acetyl-1,2,3,4-tetrahydronaphthalene, available under the trademark "TONALID", 1,3,4,6,7,8-hexahydro-4,6,6,7,8,8-hexamethylcyclopenta-2-benzopyran, available under the trademark "GALAXOLIDE", 2-n-heptylcyclopentanone, 3a,4,5,6,7,7a-hexahydro-4,7-methano-1(3)H-inden-6-ylpropionate, available under the trademark "FLOROCYCLENE", 3a,4,5,6,7,7a-hexahydro-4,7-methano-1(3)H-inden-6-ylacetate, available under the trademark "JASMACYCLENE", 4-(4'-hydroxy-4'-methylpentyl)-3-cyclohexenecarbaldehyde, alpha-hexylcinammic aldehyde, heliotropin, Hercolyn D, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoamyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, LRG 201, 1-menthol, 2-methyl-3-(p-isopropylphenyl)propanal, 2-methyl-3-(p-t-butylphenyl)propanal, 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, Musk ambrette, myrtenol, neroli oil, nonanediol-1,3-diacetate, nonanol, nonanolide-1,4, nopol acetate, 1,2,3,4,5,6,7,8-octahydro-2,3,8,8-tetramethyl-2-acetyl-naphthalene, available under the trademark "ISO-E-

SUPER", octanol, Oppoponax resinoid, orange oil, p-t-amylcyclohexanone, p-t-butylmethylhydrocinnamic aldehyde, 2-phenylethanol, 2-phenylethyl acetate, 2-phenylpropanol, 3-phenylpropanol, para-menthan-7-ol, para-t-butylphenyl methyl ether, patchouli oil, pelargene, petitgrain oil, phenoxyethyl isobutyrate, phenylacetaldehyde diethyl acetal, phenylacetaldehyde dimethyl acetal, phenylethyl n-butyl ether, phenylethyl isoamyl ether, phenylethylphenyl acetate, pimento leaf oil, rose-d-oxide, Sandalone, styrallyl acetate, 1,1,4,4-tetramethyl-6-acetyl-7-ethyl-1,2,3,4-tetrahydronaphthalene, available under the trademark "VERSALIDE", 3,3,5-trimethyl hexyl acetate, 3,5,5-trimethylcyclohexanol, terpineol, terpinyl acetate, tetrahydrogeraniol, tetrahydrolinalool, tetrahydromuguol, tetrahydromyrcenol, thyme oil, trichloromethylphenylcarbinyl acetate, tricyclodecenyl acetate, tricyclodecenyl propionate, 10-undecen-1-al, gamma undecalactone, 10-undecen-1-ol, undecanol, vanillin, vetiverol, vetiveryl acetate, vetyvert oil, acetate and propionate esters of alcohols in the list above, aromatic nitromusk fragrances, indane musk fragrances, isochroman musk fragrances, macrocyclic ketones, macrolactone musk fragrances, and tetralin musk fragrances.

Perfumes frequently include solvents or diluents, for example: ethanol, isopropanol, diethylene glycol monoethyl ether, dipropylene glycol, diethyl phthalate and triethyl citrate.

Perfumes which are used in this invention may, if desired, have deodorant properties as disclosed in U.S. Pat. No. 4,303,679, U.S. Pat. No. 4,663,068 and EP-A-545556.

If the polymer particles are solid particles which are impregnated with perfume after manufacture, we have found that the absorption of perfume can be enhanced by choosing perfumery materials with a hydrophobic character or mixing a hydrophobic oil into the perfume. Examples of hydrophobic oils which can enhance perfume uptake are dibutylphthalate, alkane mixtures such as isoparaffin and di($C_8$–$C_{10}$ alkyl) propylene glycol diester.

Perfume Properties

When the preferred solid particles are allowed to absorb perfume, they can absorb a surprising quantity, often in excess of their own weight.

We prefer to use a polymer:perfume weight ratio in a range from 4:1 to 1:10, especially from 2:1 or 3:2 up to 1:3 or 1:4.

When perfume is encapsulated in microcapsules, for instance capsules of aminoplast resin, the weight ratio of shell polymer to perfume may lie in a range from 1:30 or 1:20 to 1:2 or 1:1.

Perfume Release

If the polymer particles are solid particles impregnated with perfume, then after deposition of the particles onto a surface, such as fabric surface, hair, skin, glass etc, the perfume will be released from the surface by evaporation from the particles. We have observed that the profile of evaporation from the particles is similar to the profile of evaporation from neat perfume oil itself. As is usual, the more volatile "top note" materials evaporate first. In consequence the character of the fragrance is not greatly changed by absorption into the polymer particles.

However, we have observed that some perfume components are retained in the deposited particles during the drying, whereas they are lost by evaporation during drying if deposited directly on fabric without polymer present. Thus the polymer particles may alter the character of the fragrance retained on a surface after drying, so that it more closely resembles the original perfume oil.

If the polymer particles are capsules containing liquid perfume, the perfume may be trapped within the capsules until the capsules rupture (although we prefer capsules with a thin wall, to allow the perfume to diffuse out through the intact wall). Rupture of capsules may take place during drying, notably during tumble drying of fabrics, or it may take place during handling and ironing of fabrics.

Fabric Detergent Composition

Perfume-carrying particles of this invention may be incorporated into a detergent composition for fabric washing. Such a composition may be in solid form, notably a particulate or compressed solid composition, or may be in liquid form, notably with an aqueous or non-aqueous liquid phase with or without suspended solid.

Surfactants useful as detergent active in the detergent compositions herein include well-known anionic, nonionic, amphoteric and zwitterionic surfactants. Typical of these are the alkyl benzene sulphonates, alkyl sulphonates, alkyl- and alkyl ether sulphates, primary alkyl sulphates, alkoxylated alcohols, alpha-sulphonates of fatty acids and of fatty acid esters, alkyl betaines, and alkyl polyglycosides all known in the detergent art.

Detergent active is preferably present in a quantity of at least 5% or 10% by weight of a composition, and may well be in a quantity not exceeding 50% or 40% by weight. Concentrated solid detergent compositions will generally contain detergent active in a quantity from 10% to 50% by weight of the composition. Liquid compositions will typically contain from 5% to 30% by weight surfactants.

Detergency builders are materials which function to soften hard water by solubilisation or other removal of calcium and to a lesser extent magnesium salts responsible for water hardness compounds, especially exemplified by sodium tripolyphosphate. A further water soluble inorganic builder compound is sodium carbonate which is generally used in conjunction with a seed crystal to accelerate the precipitation of calcium carbonate. Common insoluble inorganic detergency builders are zeolites. Organic detergency builders such as sodium citrate and polyacrylate can also be used. The detergency builder component of a detergent composition will as mentioned generally comprise from 5 to 80%, preferably from 5 to 10% to 60% by weight of the detergent composition. As is well known, many detergent compositions avoid phosphate builders.

A liquid composition will typically contain 5% to 40% by weight of water-soluble builder salt, partially dissolved and partially suspended in an aqueous liquid phase.

Other ingredients which are customarily included in a detergent composition, although not necessarily all together, include bleaches, bleach activators, alkaline silicate, soil release agents, anti-redeposition agents such as sodium carboxymethyl cellulose, enzymes, fabric softening agents including softening clays, fluorescent brighteners, antifoam agents or conversely foam boosters and filler such as sodium sulphate.

A detergent composition will generally contain from 0.1 to 3% by weight of perfume, more usually not over 1.5% or 1%, at least partially carried by perfume particles according to this invention. Perfume carrying particles of this invention are preferably added to a detergent composition after any manufacturing steps involving heat (e.g. spray drying).

Thus perfume carrying particles according to this invention may be added to a detergent composition, typically by mixing them into the preformed particulate or liquid detergent composition. They may be added as dry particles, or as an aqueous slurry. If the composition is a particulate solid, the water content of a slurry may be absorbed by other constituents of the detergent composition.

Fabric Conditioners

Perfume-carrying particles may be incorporated in fabric conditioning products used during rinsing of fabrics. The main benefits delivered by such products are softness, fragrance and anti-static. Softness is usually the most important.

A fabric softening product contains at least one softening agent which functions to give the fabric a softer handle. Frequently such agents also provide an anti-static benefit. Such agents are usually cationic, but may be nonionic, amphoteric or zwitterionic materials.

Many fabric softening products take the form of compositions intended to be added to rinse water. The fabric softening agents are then materials with low solubility in water, and which deposit on the fabrics. Typically the solubility in acidified water at 20° C. is less than 10 g/litre, preferably less than 1 g/litre. When added to rinse water such materials form a dispersed phase which is then able to deposit on fabrics which are being rinsed in the water.

Many commercially important fabric softening agents are organic compounds containing quaternary nitrogen and at least one carbon chain of 6 to 30 carbon atoms, e.g. in an alkyl, alkenyl or aryl substituted alkyl or alkenyl group with at least six aliphatic carbon atoms.

Other fabric softening agents are the corresponding tertiary amines and imidazolines, other aliphatic alcohols, esters, amines or carboxylic acids incorporating a C8 to C30 alky, alkenyl or acyl group, including esters of sorbitan and esters of polyhydric alcohols, mineral oils, polyols such as polyethylene glycol, and also clays.

Some specific instances of fabric softening agents are:
1) Acrylic quaternary ammonium compounds of the formula (I)

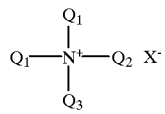

(I)

wherein each $Q_1$ is a hydrocarbyl group containing from 15 to 22 carbon atoms, $Q_2$ is a saturated alkyl or hydroxy alkyl group containing from 1 to 4 carbon atoms, $Q_3$ may be as defined for $Q_1$ or $Q_2$ or may be a phenyl and $X^-$ as an anion preferably selected from halide, methyl sulphate and ethyl sulphate radicals.

Throughout this discussion of fabric softening agents the expression hydrocarbyl group refers to alkyl or alkenyl groups optionally substituted or interrupted by functional groups such as —OH, —O—, —COHN—, —COO—, etc.

Representative examples of these quaternary softeners include ditallow dimethyl ammonium chloride; ditallow dimethyl ammonium methyl sulphate; dihexadecyl dimethyl ammonium chloride; di(hydrogenated tallow) dimethyl ammonium methyl sulphate or chloride; di(coconut) dimethyl ammonium chloride dihexadecyl diethyl ammonium chloride; dibenhenyl dimethyl ammonium chloride.

Examples of commercially available materials in this class are ARQUAD 2C, ARQUAD 2HT, ARQUAD 2T (all Ex Akzo Chemie) and PRAPAGEN WK, PRAPAGEN WKT, DODIGEN 1828 (all Hoechst).
2) Diamido Quaternary Ammonium Salts
Diamido quaternary salts of general formula (III) are also known to be useful as fabric softening agents.

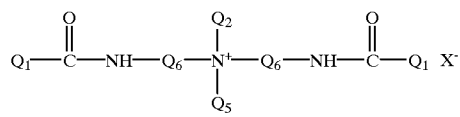

(III)

$Q_6$ is a divalent alkylene group containing from 1 to 3 carbon atoms. $Q_1$, $Q_2$, $Q_5$ and $X^-$ are as defined previously.

Examples of suitable materials are methylbis (tallowamidoethyl)(2-hydroxyethyl) ammonium methyl sulphate and methyl bis (hydrogenated tallowamido ethyl)(2 hydroxyethyl) ammonium methyl sulphate. These materials are available from Sherex Chem Co under trade names VARISOFT 222 and VARISOFT 110 respectively and under the trade name ACCOSOFT from Stepan.
3) Ester Quaternary Ammonium Salts
A number of ester groups containing quaternary ammonium salts, including those disclosed in EP 345842 A2 (Procter), EP 239910 (Procter) and U.S. Pat. No. 4,137,180 (Lever) and incorporated herein by reference, are known to be particularly useful as softening materials. These materials can be represented by generic formulae (IV) and (V) below.

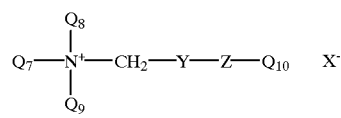

(IV)

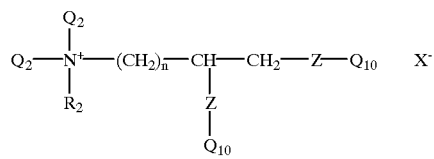

(V)

In formula (IV) $Q_7$ is a hydrocarbyl group containing 1 to 4 carbon atoms, $Q_8$ is $(CH_2)_n$—Z—$Q_{10}$ where n is an integer from 1 to 4 or —$Q_{10}$. $Q_9$ is an alkyl or hydroxyalkyl group of 1 to 4 carbon atoms, or is as defined for $Q_8$. $Q_{10}$, is a hydrocarbyl group containing from 12 to 22 carbon atoms and Y can be —CH(OH)—CH$_2$— or $Q_6$, as previously defined. Z can be —O—C(O)O—, —C(O)O—C(O)—O or —O—C(O)— and $X^-$ is an anion.

In formula (V) the symbols $Q_2$, $Q_{10}$, Z and $X^-$ have the meanings defined previously.

Suitable materials of formula (IV) are N,N-di (stearyl-oxyethyl)-N,N-dimethyl ammonium chloride and N,N-di (stearyl-oxyethyl)-N-hydroxyethyl-N-dimethyl ammonium chloride. Stearyl may be replaced with oleyl, palmityl or tallowyl (mixed chain length) groups. An illustrative example of a formula (V) material is 1,2-ditallowyloxy-3-trimethyl ammoniopropane chloride, which is a ditallow ester of 2,3-dihydroxy propane trimethyl ammonium chloride (HOECHST).
4) Quaternary Imidazolinium Salts
A further class of cationic softener materials is the imidazolinium salts of generic formula (VI).

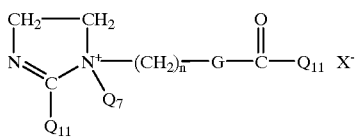

(VI)

Wherein $Q_{11}$ is a hydrocarbyl group containing from 6 to 24 carbon atoms, G is —N(H)—, or —O—, or $NQ_2$, n is an integer between 1 and 4, and $Q_7$ is as defined above.

Preferred imidazolinium salts include 1-methyl-1-(tallowylamido) ethyl-2tallowyl-4,5 dihydro imidazolinium methosulphate and 1-methyl-1-(palmitoylamido) ethyl-2-octadecyl-4,5-dihydroimidazolinium chloride. Representative commercially available materials are VARISOFT 475 (Sherex) and REWOQUAT W7500 (Rewo).

5) Zwitterionic Fabric Softeners

Other useful ingredients of softening systems include zwitterionic quaternary ammonium compounds such as those disclosed in EP 332270 A2 (Unilever) incorporated herein by reference. Representative materials in this class are illustrated by general formula (XI) and (XII)

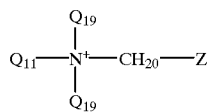

(XI)

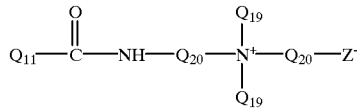

(XII)

wherein the groups $Q_{19}$ are selected independently from $Q_7$, $Q_{11}$ and $Q_{14}$; $Q_{20}$ is a divalent alkylene group containing 1 to 3 carbon atoms and may be interrupted by —O—, —COHN, —C(O)O—, etc; and $Z^-$ is an anionic water solubilising group (e.g. carboxy, sulphate, sulpho or phosphonium).

Examples of commercially available materials are the EMPIGEN CD and BS series (Albright Wilson) the REWO-TERIC AM series (Rewo) and the Tegobetain F, H, L and N series (GOLDSCHMIDT).

6) Nonionic Ingredients

It is well known to blend nonionic materials with cationic, amphoteric or zwitterionic softening materials as a means of improving dispersion of the product in rinse waters and enhancing the fabric softening properties of the softener blend.

Suitable nonionic adjuncts include lanolin and lanolin derivatives, fatty acids containing from 10 to 18 carbon atoms, esters or fatty acids containing from 8 to 24 carbon atoms with monohydric alcohols containing from 1 to 3 carbon atoms, and polyhydric alcohols containing 2 to 8 carbon atoms such as sucrose, sorbitan, together with alkoxylated fatty acids, alcohols and lanolins containing an average of not more than 7 alkylene oxide groups per molecule. Suitable materials have been disclosed in EP-A-88520 (Unilever), EP-A-122141 (Unilever), GB 2157728A (Unilever), GB 8410321 (Unilever), EP-A-159918 (Unilever), EP-A-159922 (Unilever) and EP-A-79746 (Procter).

Fabric softening compositions generally do not contain anionic detergent active nor bleach, nor detergency building.

It is desirable that the amounts (if any) of anionic detergent active, bleach and detergency builder are all less than the amount of the fabric softening agent.

A fabric softening composition which is intended to be added to rinse water may be in the form of a solid, a powder or tablet for instance, which disperses in the rinse water.

More commonly, a fabric softening composition for addition to rinse water is in the form of a liquid, and is an aqueous dispersion in water. Such a fabric softening composition may contain from 1% or 2% up to 30% or 40% by weight of a fabric softening agent but may contain higher levels from 40% up to 80% or even 90% by weight in a very concentrated product. The composition will usually also contain water, which may provide the balance of the composition.

Liquid fabric softening compositions are customarily prepared by melting the softening ingredients and adding the melt to hot water, with agitation to disperse the water-insoluble ingredients.

Perfume-carrying particles according to this invention may be added as dry particles or as an aqueous slurry, suitable after the composition has cooled.

The amount of perfume incorporated in a fabric softening product will lie in the range from 0.01% to 10% by weight.

For fabric conditioning liquids containing less than 40% by weight of fabric softening agent, the amount of perfume is preferably 0.1 to 3% by weight, more preferably 0.1 to 1.5%.

Another form of fabric softening product has a fabric softening agent in a composition which is coated onto a substrate, usually a flexible sheet or sponge, which is capable of releasing the composition in a tumble dryer. Such a product can be designed for single usage or for multiple uses. One such multi-use article comprises a sponge material releasably enclosing enough of the conditioning composition to effectively impart fabric softness during several drying cycles. The multi-use article can be made by filling a porous sponge with the composition. In use, the composition melts and leaches out through the pores of the sponge to soften and condition fabrics. A single use sheet may comprise the inventive compositions carried on a flexible substrate such as a sheet of paper or woven or non-woven cloth substrate. When such an article is placed in an automatic laundry dryer, the heat, moisture, distribution forces and tumbling action of the dryer removes the composition from the substrate and deposits it on the fabrics. Substrate materials for single use and multiple use articles, and methods of impregnating or coating them are discussed in U.S. Pat. No. 5,254,269 and elsewhere.

A fabric softening product which is an impregnated or coated sheet, sponge or other substrate will typically contain perfume-carrying particles in a quantity to provide from 0.5 to 8% by weight perfume, preferably from 2% or 3% up to 6%.

Personal Washing Products

Perfume-containing particles can be utilised in soap bars and in so-called syndet bars which contain non-soap detergent active, but are used for personal washing. Sodium fatty acyl isethionate is commonly used in this context. In such products the particles may provide from 0.5 to 5% by weight perfume.

Perfume-containing particles can be utilised in liquid products for personal washing, such as hair shampoos or shower gels. These typically contain from 2 to 40% by weight of detergent active which is anionic, amphoteric, nonionic or a mixture of these, especially a mixture in which anionic and/or amphoteric detergent active provides 2 to 40% by weight of the composition.

Such products will frequently include other materials, especially 0.01 to 3% by weight of cationic polymer (for example polyquartenium-10polyquartenium-39 and guer-hydroxypropyl-trimonium chloride) and/or 0.1 to 10% by weight of silicone to deposit on skin or hair.

Again in such products the particles may provide from 0.5 to 5% by weight perfume.

Preferably such liquid compositions will be of desirable viscosities, so as to be pourable or squeezable, and yet will not be so thin that they run uncontrollably. The desired viscosity range is approximately 1,000 to 15,000 centipoises at room temperature (25° C.) and low shear rate, preferably 3,000 to 6,000 centipoises at 10 sec$^{-1}$ shear rate.

Household Cleaning Products

The perfume-containing particles of the present invention can also be utilised in household products for cleaning hard surfaces. These are usually aqueous liquids containing detergent active and, frequently, polymeric thickener. Other common ingredients are solvents and bleach. The amount of detergent active which is used may vary widely. For some products a low level such as 0.5–3% is appropriate, while others may have more, ranging up to 15% or 20% by weight. Product viscosity will frequently exceed 100 centipoise at 10 sec$^{-1}$ shear rate and a range of 200 to 2000 centipoise at 10 sec$^{-1}$ shear rate is common.

Hair-Conditioning Products

The perfume-containing particles of the present invention can also be utilized in products used for hair conditioning. These products are usually aqueous liquids containing a range of materials designed to improve the shine, body and manageability of the hair, the hair conditioning agents being present at 2–60%, typically 2–10%. The conditioning materials consist of non-ionic, amphoteric or cationic polymers (for example hydroxyethyl cellulose, polyquarternium-39, guar hydroxypropyl-trimonium chloride, polyquarternium-10 and quaternised keratin), non-ionic, cationic and amphoteric surfactants (for example stearyl dimethyl benzyl ammonium chloride, ethoxylated fatty alcohols, ethoxylated esters of fatty alcohols and cetyl trimethyl ammonium bromide) and oils and waxes (for example cetearyl alcohol, silicone oils, mineral oils, natural oils such as avocado and jojoba oils, and glycerol esters). Suitable hair conditioners may also contain other ingredients, including solvents, vitamins, hair nourishing ingredients, dyes, preservatives and pH control agents. The products have a range of viscosities from 100 centipoise at 10s$^{-1}$ shear rate up to and exceeding 2000 centipoise at 10s$^{-1}$ shear rate, depending on the desired product form and mode of application. Hair conditioners can be designed either to be left on the hair after use or to be rinsed out. The products are typically perfumed at levels between 0.3 and 5%, preferably 0.3–1%.

The invention will be further explained and exemplified by the following Examples in which all parts and percentages are by weight, unless stated otherwise.

EXAMPLE 1

A 700 ml reaction flask equipped with motorised stirrer, reflux condenser, thermometer and inlet tube for delivery from a peristaltic pump was placed in a water bath at about 65° C.

An aqueous phase was prepared by mixing hydroxyethyl cellulose (5 parts) and deionized water (168 parts). The hydroxyethyl cellulose had a degree of substitution of one and was available from Hercules Chemical Corp as NATROSOL 250L. This phase was mixed until the hydroxyethyl cellulose dissolved and was then charged into the reaction flask. Stirring was applied to the reaction flask.

A monomer phase was prepared by mixing iso-butyl methacrylate (70 parts) with a cross linking co-monomer which was 1,6-hexanedioldiacrylate (1.8 parts).

2,2'-azo(bis)isobutyronitrile (usually abbreviated to AIBN) (2 parts) was added directly to the reaction flask and dispersed for about five minutes.

The monomer phase was added to the stirring reaction flask using a peristaltic pump over about ninety minutes. After addition the reaction mass was stirred at about 65° C. for about three hours and subsequently cooled.

The polymer beads were recovered from the aqueous slurry by filtration and air dried. The beads were sieved to separate the fraction with size below 125 µm.

It can be seen that in this Example, the total quantity of hydroxy-functional polymer was less than 10% by weight of monomers, and only part of that quantity becomes attached to the polymer beads.

The cross linking agent is 2% by weight and 1.63% by mole of the monomer mixture.

EXAMPLE 2

A 700 ml reaction flask, equipped as in Example 1, was placed in a water bath at about 65° C.

An aqueous phase was prepared by mixing poly(vinyl alcohol) available as Gohsenol AH-22 from Nippon Gohsei British Trades and Shippers Ltd, Dagenham, Essex and having a degree of hydrolysis of 97 to 98.8% (5 parts) and deionized water (168 parts). This phase was stirred until the poly(vinyl alcohol) dissolved and was then charged into the reaction flask. Stirring was applied to the reaction flask.

A monomer phase was prepared by mixing styrene (68 parts) and 1,6-hexanedioldiacrylate (1.8 parts).

AIBN (2 parts) was added directly to the reaction flask and dispersed for about five minutes.

The monomer phase was added to the stirring reaction flask using a peristaltic pump over about ninety minutes. After addition the reaction mass was stirred at about 65° C. for about three hours and subsequently cooled.

At this stage, the products was in the form of an aqueous slurry from which the polymer beads were recovered by filtration and air dried.

EXAMPLES 3 to 5

The procedure of Example 2 was repeated with different monomers as follows:

Example 3: Methyl methacrylate (70 parts) and 1,6-hexanedioldiacrylate (1.8 parts)

Example 4: n-Butylmethacrylate (70 parts) and 1,6-hexanedioldiacrylate (1.8 parts)

Example 5: iso-butylmethacrylate (54 parts) and hydroxypropylmethacrylate (18 parts)

In each of these examples the monomers were satisfactorily converted to polymer beads. These were recovered by filtration and air dried.

EXAMPLE 6

Beads, produced as in Example 5, were sieved to remove any beads larger than 75 µm diameter.

A perfume was prepared consisting of equal amounts of i) dihydromyrcenol (2,6-dimethyl-7-octen-2-ol)
ii) anisaldehyde
iii) dimethylbenzylcarbinyl acetate
(iv) 1,1,2,4,4,7-hexamethyl-6-acetyl-1,2,3,4-tetrahydronaphthalene, available under the trademark "TONALID",
(v) 3a,4,5,6,7,7a-hexahydro-4,7-methano-1(3)H-inden-6-ylpropionate, available under the trademark "FLOROCYCLENE", Perfume-loaded polymer beads were prepared by mixing the above beads and perfume into a diluted rinse conditioner, to yield an aqueous slurry containing:

| | |
|---|---|
| Polymer beads | 10.71% |
| Perfume | 10.71% |
| Dihardened tallow dimethyl ammonium chloride | 3.5% |
| Water | Balance |

This slurry was agitated for two hours and left to stand for twenty four hours, after which it appeared that all the perfume had been absorbed into the polymer beads.

This slurry was added to a quantity of a rinse conditioner formulation which was an aqueous emulsion containing a 1,2-dihardened tallowloxy-3-trimethyl ammoniopropane chloride (HTTMAPC) as cationic softener. This material is disclosed in U.S. Pat. No. 4,137,180.

The formulation contained:

| | |
|---|---|
| HTTMAPC (including some fatty acid impurity) | 13.5% |
| Ethoxylated Coconut alcohol (20EO) | 0.75% |
| Hardened tallow alcohol | 0.75% |
| Calcium chloride | 0.2% |
| Preservative | 0.02% |
| Demineralised water | Balance to 100% |

After adding the slurry, the resulting perfumed formulation contained 0.75% by weight perfume, carried in polymer beads. The perfumed rinse conditioner formulation was agitated for two hours and then stored for six days in a closed container. A control formulation contained 0.75% by weight perfume, and the same concentration of fabric softener, without polymer beads.

To test perfume deposition, this rinse conditioner formulation and the control formulation were both diluted with water to provide rinse liquors containing 0.5% of the rinse conditioner formulation.

Test pieces of fabric were de-sized cotton terry towelling, approximate weight 25 g. For each test, a piece of terry towelling was weighed accurately and treated with 30 times its own weight of rinse liquor, in a Tergotometer pot, stirring at 80 rpm for 20 minutes. The cloth was then wrung out by hand, and line dried.

The amount of perfume in the fresh and used rinse liquors was determined by solvent extraction from 100 g of rinse liquor and gas chromatographic (GC) analysis of the solvent extract. The percentage deposition of perfume materials onto the cloth was calculated for three of the five materials. The results obtained were:

| | % Deposition | |
|---|---|---|
| Ingredient | Control | Perfume in polymer beads |
| Dihydromyrcenol | 14 | 25 |
| DMBCA | 24 | 33 |
| Florocyclene | 38 | 42 |

The amount of perfume on the dry cloth was determined by extraction of 5 g of dry cloth with 20 ml ethyl acetate, followed by GC analysis of the solvent extract.

The amount of perfume detected was expressed as a percentage of the theoretical maximum quantity (which would be present if there were complete deposition onto fabric and no subsequent losses).

The results obtained for materials were:

| | % Ingredient remaining on dry cloth | |
|---|---|---|
| Ingredient | Control | Perfume in polymer beads |
| Dihydromyrcenol | not detected | 1.3 |
| DMBCA | not detected | 8.0 |
| Florocyclene | not detected | 9.8 |
| Tonalid 2 | 30.2* | 51.1* |

* = result possibly affected by other GC peaks.

EXAMPLE 7

Perfume mixture was incorporated into polymer beads, as set out in the previous Example, but with two ratios of polymer to perfume. These were 1:1 polymer to perfume and 1:2 polymer to perfume.

The resulting perfumed beads were incorporated into rinse conditioner formulations as in the previous example so as to provide 0.75% by weight perfume in each formulation. A control formulation contained 0.75% by weight perfume, but no polymer. These were diluted to rinse liquors containing 0.5% by weight fabric conditioner, and used to treat terry towelling as in the previous Example.

The treated cloths were assessed by a panel of eight people.

Assessments were made on damp cloth directly after treatment, on dry cloth 24 hours after treatment and on dry cloth five days after treatment.

The assessments were:

| Assessment Stage | Control (no polymer) | 1:1 polymer to perfume | 1:2 polymer to perfume |
|---|---|---|---|
| Damp Cloth | Strongest | Weaker than control Equal to (1:2) | Weaker than control Equal to (1:1) |
| Dry Cloth (24 hours) | Intense Tonalid odour | Florocyclene, Tonalid and anisaldehyde odours Stronger than (1:2) | Florocyclene, Tonalid and anisaldehyde odours Weaker than (1:1) |
| Dry Cloth (five days) | Tonalid odour | Florocyclene, Tonalid and | Florocyclene, Tonalid and |

-continued

| Assessment Stage | Control (no polymer) | 1:1 polymer to perfume | 1:2 polymer to perfume |
|---|---|---|---|
| | | anisaldehyde odours Weaker than (1:2) | anisaldehyde odours Stronger than (1:1) |

EXAMPLE 8

Beads were produced as in Example 2. The monomer mixture was isobutyl methacrylate (70 parts) mixed with 1,6-hexanedioldiacrylate (1.8 parts). Preparations were carried out using various different grades of polyvinyl alcohol and some other materials as the stabiliser. The grades of polyvinyl alcohol differed in the extent to which they had been hydrolysed from polyvinyl acetate.

The materials used were:

| | Stabiliser | Hydrolysis | Tradename |
|---|---|---|---|
| A | polyvinyl alcohol | 98–99% | Gohsenol N-300 |
| B | polyvinyl alcohol | 97–98.5% | Gohsenol A-300 |
| C | polyvinyl alcohol | 87–89% | Gohsenol GH-23 |
| D | polyvinyl alcohol | 78–80% | Gohsenol KH-17 |
| E | polyvinyl alcohol jointly with a surface active acrylamide copolymer | 97–99% | Gohsenol AH-22 |
| F | polyvinyl alcohol jointly with a 95:5 copolymer of acrylamide and behenyl (25 ethylene oxide) methacrylate | 97–99% | Gohsenol AH-22 |
| G | hydroxyethyl-cellulose | | Natrosol 250L |
| H | surface active acrylamide copolymer (comparative example) | | MER 10 |

In all cases the dried beads were mixed with their own weight of a single perfumery material, Florocyclene, also used in Example 6. After mixing they were left to equilibrate overnight, then a small quantity of finely divided silica (2% based on the total weight of perfume and polymer) was added as a surface improving flow aid.

The perfume-containing polymer beads were mixed into rinse conditioner (as used in Example 6) using a magnetic stirrer. In each case the amount of perfume carrying beads was 1.5% by weight of the rinse conditioner, so that the quantity of perfume was 0.75% by weight of the rinse conditioner formulation. A control formulation was prepared containing 0.75% Florocyclene without the polymer.

Deposition onto fabric was assessed using test cloths made of cotton terry towelling, acrylic fabric, and polyester. The fabric washing procedure was the same as set out in Example 6. After treatment of the fabric and drying, the intensity of Florocyclene on groups of the dried test cloths was assessed by a panel of five assessors who ranked the cloths in order of intensity of Florocyclene. The following results were obtained as unanimous views of the assessors:

On cotton test pieces B > A > C > Control
C > D > Control
E > F > Control
and G > H > Control
On acrylic test pieces A > B > C > Control On polyester test pieces A,B and C were all stronger than the control, but the assessors were not unanimous as to which of the three gave the highest perfume intensity.

These results demonstrate that the polymer particles A,B,C and D made using polyvinyl alcohol as stabiliser and hydroxy-functional monomer all gave an increase in the perceived intensity of perfume on fabric. So did polymer particles E and F made using polyvinyl alcohol in a mixture of stabilisers. The polymer particles G made using hydroxyethylcellulose as stabiliser and hydroxy-functional monomer also gave an increase in the perceived intensity of perfume on fabric and were superior to the particles H made using a different polymer as stabiliser.

EXAMPLE 9

Polymer beads were prepared by the procedure of Example 2, using isobutyl methacrylate as the sole monomer, without cross-linking agent.

Polymer beads (0.6% by weight) and dimethyl dibenzyl carbinyl acetate (DMBCA) (0.6% by weight) were added to a rinse conditioner formulation (as in Example 6). A control formulation contained 0.6% by weight of DMBCA, but no polymer beads.

After mixing the formulations, they were left in sealed containers for one week to equilibrate.

To test perfume deposition, the rinse conditioner formulation and the control formulation were both diluted with water to form rinse liquors containing 0.3% by weight of the formulation.

These liquors were used to wash terry towelling test pieces, as in Example 6. After drying, the test pieces were assessed for intensity of DMBCA by a panel of seven assessors. They unanimously considered that the DMBCA was present on the cloth with more intensity when polymer beads were used, compared with the control where no polymer beads were used.

The same result was obtained using phenylethyl isoamyl ether, available under the trade mark ANTHER, in place of DMBCA.

The same result was also obtained using FLOROCYCLENE, as referred to in Example 6, in place of DMBCA.

In a similar procedure the rinse conditioner was dosed with 0.6% polymer beads and 0.2% of FLOROCYCLENE. The control formulation was dosed with 0.6% FLOROCYCLENE only. When the dried test pieces were assessed, the perfume intensity on the cloth from 0.2% FLOROCYCLENE plus 0.6% polymer beads was greater than the intensity from 0.6% FLOROCYCLENE without polymer beads.

Stability of a preferred rinse conditioner was also tested.
A perfume contained equal weights of
hexanal
d-limonene
phenylethyl alcohol
anisic aldehyde dimethyl benzylcarbinyl acetate 2,6,6-trimethyl cyclohexadiene carboxylate (ethyl safranate)

5-ethoxycarbonyl-6-isopropyl bicyclo [2,2,1] hept-2-ene (herbanate)

alkyl cyclohexyl propionate 2,2-dimethyl-3(p-ethylphenyl)propanol (floralozone)

This perfume was mixed with and absorbed into polymer beads as above, also into beads as in Example 8G. The weights of polymer and perfume were equal.

The perfume-loaded beads were mixed into a rinse conditioner formulation as used in Example 6, so as to incorporate 0.75% by weight perfume. As a control, the rinse conditioner formulation was mixed with 0.75% by weight of the perfume.

Samples were stored at room temperature of 20° C. or at 37° C. for four weeks. Then the perfume content was analysed and the condition of the products was examined. The results were

|  | Perfume remaining (wt %) | | Appearance | |
| --- | --- | --- | --- | --- |
|  | 20° C. | 37° C. | 20° C. | 37° C. |
| Control | 55.7 | 50.0 | ok | gelled |
| Example 8G | 64.7 | 52.3 | ok | viscosity increased |
| Example 9 | 66.4 | 55.3 | ok | viscosity increased |

EXAMPLE 10

A laundry detergent powder base was prepared by spray drying some of its ingredients and then adding other to give the formulation tabulated below in which percentages are based on the complete formulation.

|  | % w/w |
| --- | --- |
| Spray dried | |
| Linear alkyl benzene sulphonate | 7.00 |
| Sodium tripolyphosphate | 25.00 |
| Acrylic/maleic copolymer | 1.00 |
| Sodium silicate | 5.00 |
| Sodium sulphate | 25.00 |
| Optical Brightener | 0.20 |
| Chelant | 0.50 |
| Post-dosed | |
| Nonionic surfactant (C14–C15 E7) | 4.00 |
| Protease enzyme | 1.00 |
| Lipase enzyme | 0.30 |
| Tetraacetyl ethylene diamine (TAED) | 4.00 |
| Sodium perborate monohydrate | 16.00 |
| Sodium carbonate | 10.00 |
| Suds suppressor | 1.00 |

A perfume mixture contained equal amounts of:

2-methyl-3(para-t-butylphenyl)propionaldehyde which is available under the trademark "LILIAL", anisic aldehyde, d-limonene, dodecyl nitrile and hexyl salicylate.

This perfume mixture was mixed with an equal weight of polymer beads prepared as in Example 5. A small quantity of finely divided silica flow aid was added so as to form a free-flowing powder. This powder was then added to the laundry detergent powder base in such a quantity that the resulting composition contained 0.4% of the perfume mixture and 0.4% of the polymer beads. A control detergent powder consisted of 0.4% of this perfume mixture added directly to the above detergent powder base.

The control powder and the test powder were used to wash samples of desized cotton terry towelling by the following procedure:

The laundry powder was dissolved at a concentration of 0.7% by weight in water at 45° C. in a Tergotometer, and mixed for two minutes. Weighed samples of fabric at a wash solution to cloth ratio of 30:1 were next added to the wash liquor and washing was carried out for 20 minutes with a stirrer speed of 100 rpm. The cloths were given a single cold rinse for ten minutes at the same solution:cloth ratio, then wrung out by hand and line dried overnight.

Residual perfume was extracted from the fabric using ethyl acetate containing fluoronapthalene as an internal standard. The amounts of two materials were determined by gas chromatography into a mass spectrometer (GC-MS) and the results obtained were:

| Perfume Ingredient | Control (ng/$\mu$l) | Test (ng/$\mu$l) |
| --- | --- | --- |
| lilial | 0.44 | 5.22 |
| hexyl salicylate | 2.83 | 5.45 |

As can be seen, the use of polymer beads greatly enhanced the amount of these two perfume ingredients deposited on the fabric.

EXAMPLE 11

A liquid laundry detergent base was prepared with the following formulation:

| ingredient | % by weight |
| --- | --- |
| sodium dodecyl benzene sulphonate | 11.3 |
| sodium lauryl ether sulphate | 3.2 |
| sodium tripolyphosphate | 11.0 |
| sodium pyrophosphate | 4.0 |
| sodium carbonate | 1.75 |
| fluorescer | 0.2 |
| silicone oil antifoam | 0.5 |
| water | balance |

Polymer beads were prepared as in Examples 2 and 8. The monomer mixture was isobutyl methacrylate (70 parts) mixed with 1,6-hexanediol diacrylate (1.8 parts) as in Example 8. Preparations were carried out using two different grades of polyvinyl alcohol as the stabiliser.

The stabilisers were:

A) Polyvinyl alcohol of 87–89% hydrolysis; Gohsenol GH-23.

B) Polyvinyl alcohol of 95–97% hydrolysis; Gohsenol C-500.

Samples of these polymer beads were mixed with their own weight of FLOROCYCLENE and then the perfume impregnated beads were mixed into the laundry liquid so as to incorporate 0.4% by weight perfume. A control liquid contained the perfume added directly without polymer beads.

These liquid compositions were used to wash desized cotton terry towelling test cloths by the following procedure:

7.5 mls laundry detergent liquid was mixed with 600 mls water at 40° C. for two minutes in a Tergotometer. A 15 g piece of terry towelling was added to the Tergotometer pot and agitated in the pot for thirty minutes. The cloths were then hand wrung and line dried. Further cloths were washed in the same way, but rinsed in 600 mls cold water for two minutes before wringing and line drying.

All the cloths were assessed for FLOROCYCLENE intensity by a panel of four assessors. Assessment was carried out when the cloths were still damp and again after the cloths had been left to dry completely overnight.

At each assessment each assessor graded a control cloth and two test cloths assigning a score of 1 to the most intense, 3 to the least intense and 2 to the cloth of intermediate intensity. If two cloths could not be distinguished, both were given a halfway score, for instance 1.5 if the most and medium intensity cloths were indistinguishable. The results were averaged and are set out in the following table:

|                  | Beads A | Beads B | Control |
|------------------|---------|---------|---------|
| Damp, no rinse   | 1.5     | 1.5     | 2.75    |
| Dry, no rinse    | 2.0     | 1.0     | 3.0     |
| Damp, with rinse | 2.25    | 1.0     | 2.75    |
| Dry, with rinse  | 2.37    | 1.0     | 2.62    |

EXAMPLE 12

Polymer beads B from the previous Example were impregnated with their own weight of FLOROCYCLENE and then treated with a small amount of finely divided silica flow aid (4% of the weight of polymer) so as to produce a free-flowing powder product. These perfume impregnated polymer beads were then used in the preparation of a hard surface cleaning composition and a corresponding control formulation as set out in the following table:

|                     | Example | Control |
|---------------------|---------|---------|
| Citric acid         | 3.0     | 3.0     |
| Water               | 92.75   | 93.25   |
| Nonionic detergent C10 alcohol 7E0 | 3.0 | 3.0 |
| Xanthan gum         | 0.25    | 0.25    |
| Florocyclene        | 0.5     | 0.5     |
| Beads Ex 11B        | 0.5     | —       |

The compositions were tested by brushing 0.46 mls composition over a white ceramic tile 15 cm square. One set of tiles was left unrinsed, assessed after 1½ hours and again after leaving overnight. A second set of tiles was rinsed with 100 mils distilled water, then assessed.

Assessment was carried out by a panel of five assessors who observed that the composition with polymer beads led to a more intense odour in each comparison.

EXAMPLE 13

Polymer beads as used in Example 8G were mixed with their own weight of phenylethyl isoamyl ether (ANTHER) and then treated with finely divided silica flow aid (4% of the weight of the polymer). The resulting perfume-impregnated beads were mixed with a quaternary imidazoline fabric softener (REWOQUAT W7500/H from Sherex) so that the resulting test composition contained 4% ANTHER.

A control composition was the same quaternary softener mixed with 4% ANTHER, without polymer beads.

Test and control sheet conditioners were made by coating the test and control compositions onto non-woven fabric sheets.

Terry towelling test cloths, 20 cm×20 cm, and other laundry (to add bulk) were washed in unperfumed washing powder and then tumble dried. Each tumble dryer contained a test cloth; several items of other laundry, and a sheet impregnated with either the test or the control composition. The tumble dryers were operated on a 50 minutes programme.

After drying, the perfume odour on the terry towelling test cloths was evaluated by a panel of five people who unanimously considered that cloths dried along with the test sheets smelt strongly of ANTHER whereas there was little or no residual ANTHER smell on the cloths dried with control sheets.

EXAMPLE 14

This example illustrates improved deposition and retention of volatile perfume on hair.

A hair shampoo was prepared with the following base formulation:

| ingredient | % by weight |
|---|---|
| sodium lauryl ether sulphate | 9.6 |
| ammonium lauryl ether sulphate | 4.5 |
| sodiuin chloride | 2.0 |
| citric acid | to give pH 6.0–6.5 |
| preservative | qs |
| water | balance to 100% |

A light citrus perfume, which would not normally be substantive to hair, was prepared with the following formulation:

|  | wt % |
|---|---|
| Allyl amyl glycollate | 3.0 |
| Citrathal concentrated | 5.3 |
| Linalol | 32.0 |
| Linalyl acetate | 30.2 |
| Litsea Cubeba Oil | 3.0 |
| Orange oil | 26.5 |

Perfume beads were prepared, generally as in Example 8G, as a 27 wt % slurry in water. This slurry was sieved to exclude any beads larger than 125 µm.

The citrus perfume above was added to the slurry in an amount equal to the weight of polymer in the slurry, then mixed overnight to allow the perfume to be absorbed.

Polymer beads according to Example 8E were also prepared as an aqueous slurry, then air dried and sieved to exclude any beads larger than 125 µm. The polymer beads were mixed with finely divided silica flow aid in an amount equal to 4% by weight of the beads. The above citrus perfume was then mixed with the polymer beads to produce a mixture containing equal weights of polymer and perfume. The resulting mixture was left to stand overnight in a closed container to allow absorption of the perfume.

Perfumed shampoos were prepared by mixing the above shampoo base with either of the perfumed polymer beads in sufficient quantity that the resulting shampoo contained 1% by weight perfume. A control shampoo was prepared by mixing 1% of the citrus perfume directly into the shampoo.

The shampoos were tested on hair switches by the following procedure:

Two 12 g hair switches (Yugoslavian Red Tie) were used for each shampoo. Two aliquots, each of one gram, shampoo were measured onto watch glasses for each shampoo tested. The hair switch was wet under a running tap (~40° C., flow rate 40 ml/sec) for 5 sec, the first aliquot of shampoo was spread along the hair and massaged into the hair for 30 sec, then the switch was rinsed for 20 sec. The second aliquot of shampoo was then applied in a similar manner, massaging for 30 sec and rinsing for 30 sec. Washed switches were placed in polyethylene bags whilst other switches were washed.

The switches were evaluated for perfume intensity while damp, then when they were almost dry after 5 hours drying at room temperature, and again after 24 hours at room temperature. Evaluation was by a panel of four people who scored the switches 1,2 and 3 in order of perfume intensity. Their averaged scores are given in the following table:

|  | Control | Example 8G | Example 8E |
| --- | --- | --- | --- |
| when damp | 3 | 2 | 1 |
| after 5 hours | 3 | 2 | 1 |
| after 24 hours | 2.6 | 2.4 | 1 |

EXAMPLE 15

Perfume was encapsulated in an aminoplast resin by the following procedure:

2.5 g trimethylolmelamine condensate (Beetle resin PT336 from British Industrial Plastics Ltd) was mixed with 2.5 g of polyvinyl alcohol, 2.8 g sodium dihydrogen orthophosphate and 144.7 g water, to form an aqueous solution which was stirred in a beaker with a magnetic stirrer. The solution was adjusted to pH 4.3 with acetic acid, and then the solution was stirred at 20° C. for 90 minutes. This aqueous phase was then mixed with 60 g perfume in a Silverson Mixer and homogenised to an emulsion which was stirred for 60 minutes at room temperature. The emulsion was then stirred for 20 hours at 40° C. in a vessel with thermometer and condenser, then raised to 70° C. for three hours. After cooling, the mixture was adjusted to pH 8–10 with ammonium hydroxide. The product mixture was an aqueous slurry of aminoplast microcapsules, containing the perfume. These microcapsules incorporated the hydroxy functional polyvinyl alcohol in the aminoplast resin at the surface of the capsules, so that hydroxy groups of the polymer are available at the surface of the particles.

The capsules were incorporated into a rinse conditioner formulation as used in Example 6, so as to provide 0.75% perfume in the rinse conditioner.

In a comparative experiment, a polyacrylamide was used in place of the polyvinyl alcohol. However, addition of the resulting capsules to the rinse conditioner caused it to coagulate.

EXAMPLE 16

Acrylate polymer encapsulated within an aminoplast shell was prepared as follows:

2.5 g trimethylolmelamine condensate (Beetle resin PT336 from British Industrial Plastics Ltd) was mixed with 2.5 g of polyvinyl alcohol, a copolymer of vinyl alcohol and vinyl amine (ratio 88:12), available from Air products, 2.8 g sodium dihydrogen orthophosphate and 182.2 g water, to form an aqueous solution which was stirred in a beaker with a magnetic stirrer. The solution was adjusted to pH 4.3 with acetic acid, and then the solution was stirred at 20° C. for 90 minutes. 25 g isobutyl methacrylate, 5 g hydroxypropyl methacrylate and 30 g benzyl alcohol as solvent mixed together, and 0.6 g of an oil-soluble initiator was added, This organic solution was mixed with the aqueous solution and homogenised to an emulsion, using a Silverson Mixer. The emulsion was stirred for 60 minutes at room temperature. Next, the emulsion was stirred for 20 hours at 40° C. in a vessel with thermometer and condenser, then raised to 70° C. for three hours. After cooling, the mixture was adjusted to pH 8–10 with ammonium hydroxide. The product mixture was an aqueous slurry of aminoplast microcapsules, containing the polymer. These microcapsules incorporated the hydroxy functional polyvinyl alcohol in the aminoplast resin at the surface of the capsules, so that hydroxy groups of the polymer are available at the surface of the particles.

The slurry of polymer particles, containing about 12% of acrylate core polymer was mixed with 2-methyl-3(para-t-butylphenyl) propionaldehyde (LILIAL) in an amount equal to the weight of core polymer. The mixture was stirred for 8 hours, then allowed to equilibrate for 2 days before addition to a rinse conditioner formulation as used in Example 6, so as to provide 0.75% LILIAL in the rinse conditioner.

The resulting rinse conditioner was added at a concentration of 0.3% by weight to 600 ml water, and used to rinse a terry towelling test cloths, whose weight was measured accurately and close to 20 g. The cloth was rinsed in a tergotometer for 20 minutes, hand wrung so that the liquid-:cloth ratio was 2:1 and line dried overnight. LILIAL was extracted from the dry cloth and determined by gas chromatography.

A similar preparation and test was carried out using a copolymer with a 94:6 ratio of vinyl alcohol and vinyl amine. A control test was carried out using perfume but no polymer beads.

The weights found on the cloths were:

| | Mg/g cloth | |
| --- | --- | --- |
| | after drying overnight | 2 days later |
| Control | 1.5 | Not measured |
| beads with 88:12 copolymer | 14.7 | Not measured |
| beads with 94:6 copolymer | 17.7 | 12.6 |

Particles were prepared generally as above, using 90 g of an oil in place of the 30 g benzyl alcohol. The perfume odour was found to persist on the fabric during drying, much better than a control where the perfume was not carried by polymer particles.

EXAMPLE 17

A shower gel base was prepared with the following formulation:

|  | wt % |
|---|---|
| Sodium lauryl ether (2EO) sulphate | 16.8 |
| Coconut diethanolamide | 1.5 |
| Sodium chloride | 2.0 |
| EDTA sodium salt | 0.1 |
| Preservative | q.s. |
| Citric acid | to pH 6 to 6.5 |
| Water | balance to 100% |

A control formulation contained 1.0% by weight of a perfume, of the following composition:

|  | wt % |
|---|---|
| Dodecanal | 1.25 |
| Methylnonyl aldehyde | 2.5 |
| Allyl amyl glycollate | 1.5 |
| Anethole synthetic | 0.2 |
| Benzyl salicylate | 15.00 |
| Carvone laero | 0.1 |
| Cedramber | 4.4 |
| cis-3-hexenyl salicylate | 0.50 |
| Citronellol standard | 2.5 |
| Coumarin | 1.0 |
| Damascone alpha | 1.0 |
| Dihydro myrcenol | 12.0 |
| Dipropylene glycol | 6.38 |
| Eugenol | 0.8 |
| Tonalid | 9.0 |
| Heliotropin | 0.7 |
| Hexyl cinnamic aldehyde | 12.4 |
| Lavandin oil | 0.7 |
| Lilial | 8.0 |
| Linalol | 4.0 |
| Methyl dihydro jasrnonate | 7.0 |
| Oakmoss synthetic | 0.3 |
| Para t-butyl cyclo hexyl acetate | 6.0 |
| Patchouli oil | 2.5 |
| Undecalactone gamma | 1.2 |

A test formulation contained particles prepared as in Example 16, using 94:6 vinyl alcohol/vinyl amine copolymer prepared as in Example 16, containing the same perfume in a weight ratio of 1:1 perfume:core polymer. The formulation was prepared by including an aqueous slurry of the particles in a quantity of the shower gel base, so as to include 1% by weight of perfume.

The control and test shower gels were evaluated by the following procedure:

Washing Protocol/Evaluation:

The shower gel was applied by a second person to the subject's arms. 1 gram of each shower gel was weighed onto watch glasses. The water flow and temperature from a mixer tap was set up such that the water temperature was ~40° C. and the flow was ~100 ml/sec. The tap was left running throughout the whole experiment. The left forearm was held under the running water for ~5 seconds and the first shower gel scooped from the watch glass and applied to left forearm, keeping the arm out of the flow of water. The shower gel was lathered by rubbing it up and down the forearm for a total of 20 times, then the gel was rinsed off under the flowing tap by moving the arm up and down for a total of 10 times. The skin was patted dry with a clean towel. The whole process was then repeated for the second shower gel on the right arm.

The arms were then evaluated over time for perfume odour by a panel of four expert assessors, scoring on a scale of 0 (no perfume) to 20 (very strong perfume) as follows:

|  | Average Scores | |
|---|---|---|
| Elapsed Time | Control | Test |
| Initial | 10.0 | 12.7 |
| 1 hour | 8.5 | 10.0 |
| 3 1/2 hours | 3.2 | 5.3 |
| 6 hours | 0.3 | 2.2 |

EXAMPLE 18

For this example, polymer beads of the following composition were produced using the procedure of example 2—isobutyl methacrylate (98 parts), 1,6-hexanediol diacrylate (2 parts), the polyvinyl alcohol being Gohsenol GH-20. These yielded a 25 wt % slurry of beads with a mean particle size of approximately 25 $\mu$m into which was then stirred an equal weight of florocyclene (equal to the dry weight of the polymer) to produce the perfumed particles.

Two hair conditioning formulations were then prepared as follows:

| wt % | One | Two |
|---|---|---|
| Cetearyl alcohol | 0.9 | 0.9 |
| Stearalkonium chloride | 0.7 | 0.7 |
| Natrosol 250HHR* | 0.7 | 0.7 |
| Citric acid | 0.3 | 0.3 |
| Jaguar C13S** | 0.1 | 0.1 |
| Merquat 3331*** | 2.0 | 2.0 |
| Preservative | 0.1 | 0.1 |
| Water | to 100 | to 100 |
| Florocyclene | 0.5 | 0.5 |
| Polymer beads | — | 0.5 | ex*Hercules Inc.
**ex Chesham Chemicals
***ex Calgon Corporation

Hair switches were then treated with an equal weight of the two products and allowed to fully air dry for four hours before assessment by a panel of six assessors. All six agreed that the hair switch washed with product Two smelt significantly more strongly of florocyclene than the one washed with product One.

What is claimed is:

1. A perfumed product comprising a mixture of (1) an active ingredient selected from the group consisting of a detergent, a fabric softening agent and a hair-conditioning agent, and (2) solid particles which are insoluble in water, said particles comprising an organic polymer core which has perfume absorbed therein and having at the exterior of the core a hydroxy functional polymer attached to the core so as to form a shell at least partially about said core, said shell being permeable to perfume and said hydroxy functional polymer not being removed from the core in water, said hydroxy functional polymer incorporating free hydroxy groups and being present in a quantity which is no more than 25% of the weight of the particles.

2. A product according to or claim 1 wherein the organic polymer is a polymer of a vinyl monomer.

3. A product according to claim 2 wherein the organic polymer is a polymer of one or more monomers which are acrylic and/or alkyl acrylic esters of formula

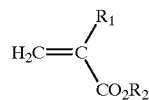

where $R_1$ is hydrogen or alkyl (including branched alkyl) of 1 to 6 carbon atoms, preferably 1 to 3 carbon atoms and $R_2$ is branched or branched alkyl of 1 to 8 carbon atoms.

4. A product according to claim 1 wherein said hydroxy functional polymer is cellulose or chemically modified cellulose.

5. A product according to claim 3 wherein $R_1$ is hydrogen or methyl, $R_2$ is alkyl (including branched alkyl) of 3 or 4 carbon atoms and said hydroxy functional polymer is polyvinyl alcohol which is at least 88% hydrolyzed from polyvinyl acetate.

6. A product according to claim 1 wherein said particles have a mean size of at least 10 μm.

7. A product according to claim 6 wherein said particles have a mean size in the range 30 to 100 μm.

8. A product according to claim 1 which is a solid laundry detergent composition for fabric washing, containing from 5 to 50% by weight of one or more detergent active compounds, and from 5 to 60% by weight of detergency builder, and from 0.1 to 1.5% by weight of perfume.

9. A product according to claim 1 which is a liquid laundry detergent composition for fabric washing, containing from 5 to 30% by weight of one or more detergent active compounds, from 5 to 40% by weight of detergency builder, water and from 0.1 to 1.5% by weight of perfume.

10. A product according to claim 1 which is a rinse conditioning liquid containing from 1 to 40% by weight of a fabric softening agent as a suspension in water, and containing 0.1 to 3% by weight perfume.

11. A product according to claim 1 which is a solid substrate impregnated or coated with a fabric softening composition, and containing from 2 to 8% perfume by weight based on the fabric softening composition.

12. A product according to claim 1 which is in the form of a bar for personal washing, wherein perfume containing particles provide from 0.5 to 5% by weight of perfume.

13. A product according to claim 1 which is in the form of a liquid for personal washing, containing 2 to 40% by weight detergent and from 0.5 to 5% by weight of perfume.

14. A product according to claim 1 which is in the form of a hair-conditioner containing 2 to 60% by weight of hair-conditioning agent(s) and 0.3 to 5% by weight of perfume.

15. A perfumed product comprising a physical mixture of (1) an active ingredient selected from the group consisting of a detergent, a fabric softening agent and a hair-conditioning agent, and (2) solid particles which are insoluble in water, said particles comprising an organic polymer core which has perfume absorbed therein and having at the exterior of the core a hydroxy functional polymer attached to the core so as to form a shell at least partially about the core, said shell being permeable to perfume, said hydroxy functional polymer not being removed from the core in water, said hydroxy functional polymer being a homopolymer or copolymer of vinyl alcohol incorporating free hydroxy groups and being present in a quantity which is no more than 25% of the weight of the particles.

16. A product according to claim 15 wherein the organic polymer is a polymer of one or more monomers which are acrylic and/or alkyl acrylic esters of formula

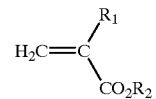

where $R_1$ is hydrogen or alkyl (including branched alkyl of 1 to 6 carbon atoms, preferably 1 to 3 carbon atoms and $R_2$ is branched or unbranched alkyl of 1 to 8 carbon atoms.

17. A product according to claim 16 wherein $R_1$ is hydrogen or methyl, $R_2$ is alkyl (including branched alkyl) of 3 or 4 carbon atoms and said further polymer is polyvinyl alcohol which is at least 88% hydrolyzed from polyvinyl acetate.

18. A product according to claim 15 wherein the polymer or copolymer of vinyl alcohol is 96 to 99% hydrolyzed.

19. A product according to claim 15 which is a solid laundry detergent composition for fabric washing, containing from 5 to 50% by weight of one or more detergent active compounds, and from 5 to 60% by weight of detergency builder, and from 0.1 to 1.5% by weight of perfume.

20. A product according to claim 15 which is a liquid laundry detergent composition for fabric washing, containing from 5 to 30% by weight of one or more detergent active compounds, from 5 to 40% by weight of detergency builder, water and from 0.1 to 1.5% by weight of perfume.

21. A product according to claim 15 which is a rinse conditioning liquid containing from 1 to 40% by weight of a fabric softening agent as a suspension in water, and containing 0.1 to 3% by weight perfume.

22. A product according to claim 15 which is a solid substrate impregnated or coated with a fabric softening composition, and containing from 2 to 8% perfume by weight based on the fabric softening composition.

23. A product according to claim 15 which is in the form of a bar for personal washing, wherein perfume containing particles provide from 0.5 to 5% by weight of perfume.

24. A product according to claim 15 which is in the form of a liquid for personal washing, containing 2 to 40% by weight detergent and from 0.5 to 5% by weight of perfume.

25. A product according to claim 15 which is in the form of a hair-conditioner containing 2 to 60% by weight of hair-conditioning agent(s) and 0.3 to 5% by weight of perfume.

* * * * *